United States Patent [19]

Totaro

[11] Patent Number: 4,664,628

[45] Date of Patent: May 12, 1987

[54] SCREENING TOOL AND PROCESS USING THE TOOL FOR A MOUTH CAVITY IN DENTAL OPERATIONS

[76] Inventor: Giuseppe Totaro, Via Fua Fusinato 24, Rovigo, Italy

[21] Appl. No.: 639,801

[22] Filed: Aug. 13, 1984

[30] Foreign Application Priority Data

Oct. 13, 1983 [EP] European Pat. Off. ........ 83830200.8

[51] Int. Cl.⁴ ............................................. A61C 5/14
[52] U.S. Cl. ..................................... 433/136; 433/96
[58] Field of Search ............... 433/137, 136, 138, 139, 433/96, 93

[56] References Cited

U.S. PATENT DOCUMENTS

| | | | |
|---|---|---|---|
| 791,563 | 6/1905 | Ludwig | 433/137 |
| 1,374,792 | 4/1921 | Woisard | 433/137 |
| 2,081,779 | 5/1937 | Titus | 433/137 |
| 2,859,518 | 11/1958 | Cohn | 433/96 |
| 3,086,289 | 4/1963 | Orsing | 433/96 |
| 3,396,468 | 8/1968 | Dayhoff | |
| 3,406,452 | 10/1968 | McConville | 433/137 |
| 4,215,477 | 8/1980 | Shanel | |
| 4,240,789 | 12/1980 | Rosenthaler | 433/136 |
| 4,259,067 | 3/1981 | Nelson | |
| 4,261,697 | 4/1981 | Newitter | 433/137 |
| 4,310,308 | 1/1982 | Oien | 433/136 |

*Primary Examiner*—John J. Wilson
*Attorney, Agent, or Firm*—McAulay, Fields, Fisher, Goldstein & Nissen

[57] ABSTRACT

An oral screening tool for use in dentistry consists of an elastic sheet pressed on three sides by an elastic two-way aspirating frame fitted to a central exhaust which includes at least one aspirator for local suction purpose. The sheet is centrally held by the tooth and, owing to its elastic nature, forms a cavity for the collection of liquids. Use of a flexible frame allows adjustment of its shape, access to the oral cavity and does not hinder breathing. The tool can be handled by a single operator and automatically performs liquid elimination.

20 Claims, 4 Drawing Figures

SCREENING TOOL AND PROCESS USING THE TOOL FOR A MOUTH CAVITY IN DENTAL OPERATIONS

BACKGROUND OF THE INVENTION

This invention relates to an oral screening tool to be applied by a dentist or technician to one or more teeth of a patient for isolating the operation or treatment zone in the mouth cavity.

More particularly, the present invention is concerned with a tool for automatically carrying out a picking up and elimination of the liquid from water jets coming from hydrical injectors of conventional tools, sucking the water from a collection cavity which the operator adjusts each time in accordance with contingent use requirements.

The screening tool is generally flexible, and this flexibility permits the operator to reach the oral cavity without being obliged to remove any dental tool or otherwise to place it so that the patient's respiration is not hindered. The possibility of isolating spittle in the mouth cavity on the side of the dental intervention permits the dentist to operate aseptically and also to prevent medication when used to enter the patient's mouth and be swallowed.

The invention also is concerned with an improved dental treatment process using the screening tool. The present procedure requires establishing points to be bored in an elastic and waterproof sheet brought in proper position on the buccal arch, then their boring and the introduction in the correct bore of a clamp with an arched spring so as to bring its inverted fin in a retention position between the spread aside periphery of the bore. The clamp holding the sheet is then conformably fitted on the tooth. The sheet is afterwards stabilized under tension in subsequent phases by tending and fixing of its edges on the tending reliefs of a stiff frame perimetrally disposed thereabout.

PRIOR ART DISCUSSION

In prior art dental treatments, operation of a dental tool and, therefore, of a water injector handled by the operator requires the presence of an assistant who has to remove liquids by means of an aspirator using steady movement. This does not prevent liquids from splashing in all directions damaging the patient's clothes and soiling the surroundings. It must be added that, in this motion, the aspiration procedure because of the aspirator interferes with the tool used by the operator; this interference may lead to a collision between these instruments and hinders the visual perception of the area to be treated.

In addition, other drawbacks are to be noted when one has to operate in the inner part of the mouth. Any frame or clamp used must be removed by unhooking it from the tooth. An apparatus which covers the mouth with a fixed structure or sheet might moreover hinder the patient's respiration, and consequently, it must be removed. The mandible movement operating on the radial tensions, in addition, unhinges the tied condition of the clamp; and, this is due to the fact that the sheet must be strongly tended on a stiff frame to allow its hinging by its elastic force.

The main object of the present invention is to avoid the above problems by means of a novel device which is directly and quickly fitted on one or more teeth by a single operator, can be changed to different positions by hand and automatically eliminates liquids.

SUMMARY OF THE INVENTION

The present tool consists of a square, a waterproof and elastic sheet contacted on three sides by a sucking device including two cannules formed by a pair of small pipes with a plurality of bores on their inner side. The sheet is air-permeable and may be formed of rubber. The sheet is sized so that it does not fit over the nose of a patient. These cannules are fixed by means of a frame of flexible metal passing through them and uniting them in the middle of the lower side of the frame below which they enter a common collector fitted on a central aspirator with one or two other aspirator tubes. All are connected to a source of suction on the dental chair.

The operator lays the assembly on the relevant dental arch part; shapes the assembly and marks one or more bores according to the number of teeth he has to treat in that phase of the procedure. The operator then chooses the clamp he deems suitable among the available ones and mounts it to the chosen bores; and, the tool is then brought in position by fitting the clamp on the tooth. The use condition of the device is obtained by spreading apart the sheet with the fingers to widen the bore and by inserting the pair of the reversed fins of the clamp into it. In mounting condition, the elastic property of the sheet centrally anchored to the tooth defines a cavity in which liquids are gathered. To adapt it to contingent use requirements, the operator can modify the disposition of the screening part by bending the flexible frame by hand in different ways. The oral cavity becomes thus thoroughly accessible by giving the screening part a valve shape. Access can be obtained by shifting the sheet free to move either to the right or to the left when it is on an arrow plane, upwards or downwards when it is on the transversal plane. This allows x-raying and anesthetizing any tooth and to do root canal work aseptically. When the instrument already fitted has to be applied to another tooth, the shape of a fishing net must be given to it so that its deepest part reaches the chosen tooth without tension. This point is marked and bored. A clamp is then mounted to the bore and fixed to the tooth by using a special tong.

For particular requirements, beside. recipheral or marginal suction, a local mobile aspirator is provided. A small pipe is fitted on the clutch of the dental chair suction source which has small bores on the sucking end and, inside it, it has a plasticized iron wire freely slidable, which allows bending and retention of the desired fitting position. For positioning, the end part of the pipe is passed around the clamp for leaving it to suck near the tooth. In case of an obstruction, the small pipe is removed, leaving the wire in the conduit to insert, as it will serve as a guide for another pipe.

To these ends, the pesent invention consists in the provision of a screening tool for the oral cavity, having a sheet of waterproof plastic material adapted to partially fit in the oral cavity, a frame adapted to fit on the sheet for retention thereof on the oral cavity, and at least one suction means associated with or included in the frame for removing liquid and solid matter from the sheet.

The invention is further concerned with a dental treatment process, which includes placing a flexible, elastic, waterproof, sheet over the oral cavity, shaping the sheet over the dental area to be treated, boring at least one opening in the sheet at a location corresponding to the area, clamping the sheet to the area through the opening, and placing a frame against the sheet, the frame including suction means whereby liquids and solids deposited on the sheet during the treatment can be removed by one person.

BRIEF DESCRIPTION OF THE DRAWING

The invention is further illustrated in non-limited fashion by the accompanying drawing wherein.

DESCRIPTION OF THE PREFERRED EMBODIMENTS

Figure 1:
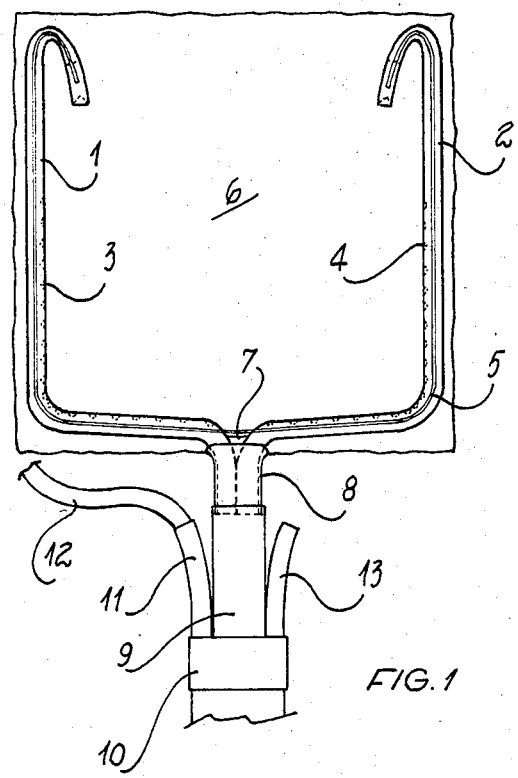
FIG. 1 is a front elevational view of the screening tool shown employing two mobile conduits for local suction.

Referring now to the drawing which illustrates the presently preferred mode for carrying out the invention, the screening tool employs a fixed lateral aspirating means comprising a pair of pipes or conduits 1 and 2 each having a hollow interior with bores 3 and 4 communicating with the hollow interior of conduits 1 and 2 respectively, and stabilized by means of a "U"-shaped frame formed of a flexible metal or iron rod 5 which passes through conduits 1 and 2 to form a flexible frame structure for supporting an integral rubber sheet 6 on three sides. In order to pass the base of the flexible frame through both conduits 1, 2 and connecting the two pipes or conduits at a low intermediate point, seal 7 is provided through which frame 5 passes. On its upper side, the integral sheet and frame structure are provided with a two-way aspirating device formed by components 1, 2, 5 and 6; the conduits 1, 2 each have their ends inwardly bent towards the sheet to provide for additional stabilization to the lower ends of the conduits.

Conduits 1, 2 have their other end which is remote from their inwardly bent ends outwardly bent to form two substantially parallel portions beyond the intermediate point at which seal 7 is provided set together in sleeve 8 which inserts them into a common collector 9 which leads to a first duct 10 fitted on the dental chair's aspirator. On duct 10, a first clutch 11 coupled with pipe 12 is mounted which can be employed for the local and mobile aspiration. For particular requirements, and to provide for further aspiration, another local or second aspiration pipe is provided together with a second clutch 13 fitted onto duct 10.

Figure 2:
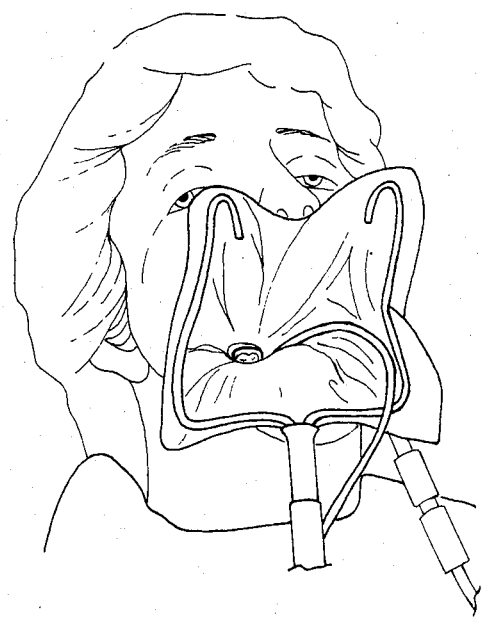
FIG. 2 is a perspective view of the same tool fitted on a tooth, and the collection cavity is formed by the elastic sheet carried or supported by a two-way suction or aspirating device held by traction on its central part by the tooth.
Figure 3:
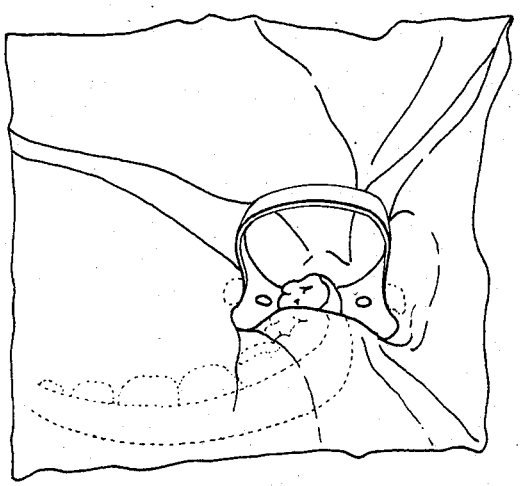
FIG. 3 is a detailed view of the clamp binding the instrument on the tooth.
Figure 4:
FIG. 4 is a perspective view of the device showing how to reach the back part of the mouth cavity without unhinging the tool.

Referring more particularly to FIG. 2, the sheet 6 is formed of rubber or flexible, preferably air-permeable plastic and of a size such that the mouth of the patient is not covered.

DESCRIPTION OF THE PROCESS

The improved dental process treatment according to the present invention comprises placing the above described sheet over the oral cavity and on a treatment area of the teeth to be treated, making at least one bore or opening in the sheet at a point corresponding to that area, clamping the sheet to the treatment area at the bore or bores; placing the aspirating frame against the sheet and aspirating liquid and solid on the sheet through the bores 3 and 4 into conduits 1 and 2, respectively as the treatment is carried out.

The details of the sucking or aspirating frame construction, the anchoring means on the teeth, the deposition of the sucking or aspirating bores, the materials and other features of the invention may be otherwise than shown.

It will be obvious to those skilled in the art that various changes and modifications may be made without departing from the scope of the invention.

I claim:

1. A screening tool for an oral cavity, comprising:
   a sheet of waterproof deformable, flexible material adapted to fit partially in the oral cavity;
   a two-way aspirating frame pressing on three sides of said sheet to retain said sheet on said oral cavity; and
   suction means associated with said frame and said sheet for removing liquid and solid matter from said sheet, said frame comprising a pair of spaced aspirating conduits connected to a source of suction on a dental chair and said conduits having deformable metal wires therein whereby said frame can be adjusted in shape.

2. The tool of claim 1 wherein said conduits have distal inlet ends bent toward one another.

3. The tool of claim 1 wherein:
   said conduits have inner ends housed in a sleeve and connected to said source of suction; and
   said tool has at least one mobile aspirating conduit fitting in said sleeve and connected to said source for local aspiration of said sheet.

4. The tool of claim 1, wherein said sheet is square and of a size such as not to cover the mouth of the patient.

5. The tool of claim 4, wherein said sheet is of a size such as not to overlap over the nose of a patient.

6. The tool of claim 1, wherein said sheet is air-permeable.

7. The tool of claim 1, wherein said sheet is of rubber.

8. The tool of claim 1, including conduits having distal inlet ends bent towards one another.

9. The tool of claim 8, wherein:
   said conduits have inner ends housed in a sleeve and connected to said source of suction; and
   said tool has at least one mobile aspirating conduit fitting in said sleeve and connected to said source for local aspiration of said sheet.

10. The tool according to claim 1, wherein each of said conduits have a plurality of bores connected to the hollow interior of said conduits for aspirating through said bores, and including a seal between said conduits through which said wire passes.

11. The tool of claim 10, wherein said sheet is square.

12. The tool of claim 11, wherein said sheet is of a size such as not to overlap over the nose of a patient.

13. The tool of claim 12, wherein said sheet is air-permeable.

14. The tool of claim 1, wherein said sheet is of plastic.

15. In a dental treatment process, the improvement comprising the combinative steps of:
   placing a flexible, elastic, waterproof sheet over the oral cavity;
   placing onto the waterproof sheet a deformable hollow pair of spaced aspirating conduits communicating with a plurality or bores placed therealong between the ends thereof, spaced between and proximate to the ends thereof;

shaping said sheet over the dental area to be treated, adjusting the conduits with a deformable means therein by bending thereof by hand to modify the shape of the sheet relative to the dental area to be treated;

boring at least one opening in said sheet at a location corresponding to said area; and aspirating dental residues through said bores;

whereby liquids and solids deposited on said sheet during said treatment can be removed by one person.

16. The improvement of claim 15, wherein said deformable means is a deformable frame provided in each of said conduits extending between the ends of each of said conduits and leaving a hollow portion between said frame and the interior of said hollow aspirating conduits.

17. The improvement of claim 15, wherein said bore is placed on at least one tooth so that said sheet is centrally held by at least one tooth and forms a cavity for collecting materials.

18. The improvement of claim 17, including centrally anchoring the sheet to the tooth.

19. A screening tool for an oral cavity, comprising:

a sheet of waterproof deformable, flexible material adapted to fit partially in the oral cavity;

a two-way aspirating flexible, but stiff frame pressing on three sides of said sheet for retaining said sheet on said oral cavity and stabilizing said sheet under tension; and suction means associated with said frame and said sheet for removing liquid and solid matter from said sheet, said frame comprising a pair of spaced aspirating conduits connected to a source of suction on a dental chair; and deformable metal wires in said conduits whereby said frame can be adjusted in shape for said stabilization thereof under tension.

20. The tool of claim 19, wherein said conduits each have one end inwardly bent towards said sheet for providing additional stabilization to the lower ends of said conduits, and the other end of each of said conduits are outwardly bent to form two substantially parallel portions beyond an intermediate point at which a seal is provided set together for insertion thereof into a common collector leading to a duct fitted on the dental chair's aspirator.

* * * * *